US010464885B2

(12) United States Patent
Lu et al.

(10) Patent No.: US 10,464,885 B2
(45) Date of Patent: Nov. 5, 2019

(54) COMPOUND, PREPARATION METHOD THEREFOR, APPLICATIONS THEREOF, CORRESPONDING TARGETED DRUG DELIVERY SYSTEM, CHEMOTHERAPY DRUGS, AND TREATMENT METHOD

(71) Applicant: BEIJING XINDE RUNXING TECHNOLOGY CO., LTD., Beijing (CN)

(72) Inventors: Xuechun Lu, Beijing (CN); Xiaohua Chi, Beijing (CN); Chengcheng Tang, Beijing (CN); Lei Shi, Beijing (CN)

(73) Assignee: BEIJING XINDE RUNXING TECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 15/779,528

(22) PCT Filed: Dec. 6, 2016

(86) PCT No.: PCT/CN2016/108717
§ 371 (c)(1),
(2) Date: May 28, 2018

(87) PCT Pub. No.: WO2017/097187
PCT Pub. Date: Jun. 15, 2017

(65) Prior Publication Data
US 2018/0346409 A1 Dec. 6, 2018

(30) Foreign Application Priority Data
Dec. 7, 2015 (CN) .......................... 2015 1 0888021

(51) Int. Cl.
| A61K 31/165 | (2006.01) |
| A61K 31/166 | (2006.01) |
| A61K 31/167 | (2006.01) |
| C07C 235/64 | (2006.01) |
| C07C 231/02 | (2006.01) |
| A61P 35/00 | (2006.01) |
| C07C 231/12 | (2006.01) |

(52) U.S. Cl.
CPC .......... *C07C 235/64* (2013.01); *A61K 31/167* (2013.01); *A61P 35/00* (2018.01); *C07C 231/02* (2013.01); *C07C 231/12* (2013.01)

(58) Field of Classification Search
CPC .. A61K 31/165; A61K 31/166; A61K 31/167; C07C 235/64; C07C 231/02; A61P 35/00
USPC .................. 514/622, 621; 564/184, 183, 182
See application file for complete search history.

(56) References Cited

U.S. PATENT DOCUMENTS

| 2006/0134724 A1 | 6/2006 | Kauppi et al. | |
| 2009/0239919 A1* | 9/2009 | Wood ..................... | C07C 235/64 |
| | | | 514/371 |

FOREIGN PATENT DOCUMENTS

| CN | 101254183 | 9/2008 |
| CN | 101537001 | 9/2009 |
| CN | 101775032 | 7/2010 |
| CN | 102010348 | 4/2011 |
| CN | 105566147 | 5/2016 |
| WO | 2012058378 | 5/2012 |

OTHER PUBLICATIONS

X Wang, Jie et al., "Design, synthesis and antitumor activity of n-butyric acid salicylanilide esters" Chinese Journal of New Drugs, vol. 22, No. 14, Jul. 29, 2013 (Jul. 29, 2013), pp. 1684-1690 and 1696.
X Yang, Yunsong et al., "Transdermal therapeutic study of niclosamide derivatives" Chinese Journal of Applied Chemistry, vol. 18, No. 12, Dec. 25, 2001 (Dec. 25, 2001) pp. 944-947.
X Yang, Y.S. et al., "Synthesis and hydrolysis study of polyacrylates containing 2', 1, 3,5-dichloro-4'-nitrosalicylanilide" Journal of Applied Polymer Science, vol. 66, No. 1, Oct. 3, 1997 (Oct. 3, 1997), pp. 29-33.
"Transdermal controlled release administration of niclosamide derivatives," Yang et al, Chinese Journal of Applied Chem istry, vol. 18 No. 12, Dec. 2001.
"Synthesis and Hydrolysis Study of Polyacrylates Containing 2* ,5-Dichloro-4*-Nitrosalicylanilide," Yang et al. Journal of Applied Polymer Science, vol. 66, 29-33 (1997).
"Design, synthesis and antitumor activity of n-butyric acid salicylanilide esters," Wang et al. Chinese Journal of New Drugs 2013, 22 (14).
"Glutamate antagonists limit tumor growth," Rzeski et al. Proceedings of the National Academy of Sciences of the United States of America, PNAS, May 22, 2001, vol. 98, No. 11, 6373.

\* cited by examiner

*Primary Examiner* — Matthew P Coughlin
*Assistant Examiner* — Sagar Patel
(74) *Attorney, Agent, or Firm* — Treasure IP Group, LLC

(57) ABSTRACT

The present invention relates to a compound and its preparation method and use and corresponding targeted drug delivery systems and chemotherapeutic drugs. The compound is a novel compound or a pharmaceutically acceptable salt thereof for treating small cell lung cancer, characterized in that, the compound has the general formula I,

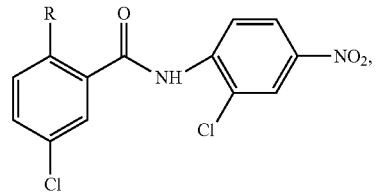

wherein R is acyloxy group. The present invention also relates to a preparation method of the compound, to use of the compound for the preparation of a chemotherapeutic drug for treating small cell lung cancer, to a targeted drug delivery system including the compound, and to a chemotherapeutic drug including the compound and for treating small cell lung cancer.

12 Claims, 8 Drawing Sheets

COMPOUND, PREPARATION METHOD THEREFOR, APPLICATIONS THEREOF, CORRESPONDING TARGETED DRUG DELIVERY SYSTEM, CHEMOTHERAPY DRUGS, AND TREATMENT METHOD

CROSS REFERENCE TO RELATED APPLICATION

This application is a national stage application of PCT/CN2016/108717, which claims priority to Chinese Application No. 201710424037.0, filed on Jun. 7, 2017. The Chinese Application and international application are incorporated herein by reference in their entireties.

TECHNICAL FIELD

The present invention belongs to the field of chemotherapeutic drugs and, specifically, relates to a pharmaceutical compound for treating small cell lung cancer and its preparation method and use and corresponding targeted drug delivery systems and chemotherapeutic drugs.

BACKGROUND ART

The incidence of small cell lung cancer (SCLC) accounts for about one-third of all lung cancers, and 10% to 15% of lung cancers, with high degree of malignancy. SCLC is featured by rapid progression and distant metastasis soon after diagnosis. Almost ⅔ of SCLC patients are at an advanced stage when diagnosed. So far, chemotherapy is still the main treatment method. Chemotherapy and radiotherapy work in patients at the initial stage; however, most patients still relapse within 2 years and die from systemic metastasis. In the past few decades, its treatment has not been significantly changed, resulting in patient's overall 5-year survival rate less than 7%. Based on a postgraduate's degree dissertation of China Medical University issued in May 2013, named as 'A retrospective study of first-line treatment of extensive-stage small cell lung cancer using topotecan as compared with etoposide plus cisplatin', it is pointed out that CAV (cyclophosphamide+doxorubicin+vincristine) treatment for small cell lung cancer has been developed into etoposide plus cisplatin chemotherapy regimen.

In recent years, researchers have tried to use multiple chemotherapy regimens and new cytotoxic drugs have been approved for treatment evaluation of relapsed SCLC, among which there are few clinically promising drugs. For patients relapsed with SCLC who are physically admissible, second-line chemotherapy and above should be given. Topotecan is the only second-line drug approved by the FDA for SCLC, however, its effectiveness is only the same as the CAV regimen. In the phase I clinical study, reported by Agelaki et al., 'A phase I clinical trial of weekly oral topo-tecan for relapsed small cell lung cancer', Cancer Chemotherapy and Pharmacology', 2013 April, 72 (1), dose-limiting toxicity (DLT) and maximum tolerated dose (MTD) of topotecan were investigated in patients with relapsed SCLC who were orally given topotecan every week. 18 Patients were orally given topotecan on Day 1, 8 and 15, lasting 28 days as a course of treatment. The initial dose was 3 mg/m$^2$, followed by an increasing dose of 0.5 mg/m$^2$ until MTD. 13 Patients underwent second-line treatment, and 5 patients underwent third-line treatment or above. The results showed that DLT appeared at 4.5 mg/m$^2$ and MTD was 4 mg/m$^2$. DLT included II-III degree neutropenia and II degree thrombocytopenia. The most common toxic side effects were II-III degree neutropenia (27.8%), II-III degree anemia (33.3%), II degree thrombocytopenia (16.7%) and II-III degree fever (44.4%). The results showed that the effectiveness of topotecan was 11.1%, the median progression-free survival (PFS) was 2.3 months, and median survival (OS) was 5.1 months. The results of this study confirmed that as the only second-line drug for treating small cell lung cancer approved by FDA, topotecan exhibited effectiveness of about 10% and may cause serious side effects on blood and bone marrow.

The combined use of different types of drugs may overcome the problem of drug resistance. Currently, progresses on targeted treatment of SCLC has been made, but so far no ideal therapeutic drug has been obtained. Currently, among drugs for clinical treatment of relapsed SCLC, except topotecan and amrubicin, most of them were not evaluated by a randomized controlled study with a large sample size. Further, although drug combination therapy is effective for a small number of patients, especially for refractory and relapsed patients, it is not suitable for patients with poor clinical status. The effectiveness is poor in refractory and relapsed patients. Even according to the Jacot research results, which provided better results than others, among 70 patients from September 1992 to August 2010, 55 patients achieved objective remission, in the meanwhile only 10% of them appeared to maintain their disease situation. The median survival time was only 3.9 months. The occurrence of III-IV degree side effects was relatively high, with the blood system involved: neutropenia (71%), thrombocytopenia (23%) and anemia (22%).

Although some researches and developments of biotargeted treatment drugs for SCLC have been conducted around the world, there has been no breakthrough progress in clinical trials and it is only theoretically suggested that there may be potential prospects in treatment of small cell lung cancer.

In summary, globally, there are no effective and efficient drugs for treating small cell lung cancer that can greatly prolong a patient's survival, much less healing. Therefore, in the field of cancer treatment and anti-tumor drug development it is urgent to develop effective and efficient drugs against small cell lung cancer that can improve the remission and survival rate of SCLC, in the field of cancer treatment and anti-tumor drug development.

SUMMARY OF THE INVENTION

In view of low efficiency of the above-mentioned treatment of small cell lung cancer and high incidence of toxic side reactions, it is urgent to develop a highly-effective low-toxicity therapeutic drug against small cell lung cancer. The present invention provides a breakthrough in new applications of known drugs and improves methods for drug synthesis. Accordingly, the inventor has surprisingly discovered a drug that is highly effective in targeted therapy of small cell lung cancer.

An embodiment of a first aspect of the present invention provides a compound or a pharmaceutically acceptable salt thereof, characterized in that the compound has the general formula I:

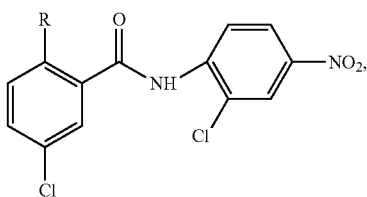

wherein R is an acyloxy group selected from acetoxy, propionyloxy or acryloyloxy. The compound can be used for treating small cell lung cancer.

In this embodiment, the molecular weight of the compound ranges from 367 to 382.

In a preferred embodiment, the acyloxy group is acetoxy.

In this embodiment, the molecular weight of the compound ranges from 367 to 368.

In this embodiment, the NMR of the compound is as follows:

$^1$HNMR (400 MHz, CDCl$_3$) δ9.03 (s, 1H), 8.85 (d, 1H, J=8.0 Hz), 8.34 (s, 1H), 8.20-8.24 (dd, 2H, J=8.0 Hz, J=4.0 Hz), 7.96 (d, 1H, J=2.4 Hz), 7.52-7.56 (dd, 2H, J=8.0 Hz, J=4.0 Hz), 7.15, 7.18 (d, 1H, J=12.0 Hz), 2.36 (s, 3H).

An embodiment of a second aspect of the present invention provides use of a compound of the general formula I or a pharmaceutically acceptable salt thereof for the preparation of a chemotherapeutic drug for treating small cell lung cancer.

In this embodiment, the chemotherapeutic drug for treating small cell lung cancer includes a targeted drug delivery system, and the targeted drug delivery system is a targeted drug carrier-encapsulated dosage form selected from liposomes, millimicro-particles, millimicro-spheres, micro-particles, nano-particles, complex emulsions, or solid lipid nano-particles.

An embodiment of a third aspect of the present invention provides a targeted drug delivery system characterized by including a pharmaceutically effective amount of a compound of the general formula I or a pharmaceutically acceptable salt thereof, and the targeted drug delivery system is a targeted drug carrier-encapsulated dosage form selected from liposomes, millimicro-particles, millimicro-spheres, micro-particles, nano-particles, complex emulsions, or solid lipid nano-particles. The pharmaceutically effective amount of the drug may be determined by a person skilled in the art according to patient's conditions, being in the range of 0.5-2 g/day, optionally in the range of 0.55-1.95 g/day, or the range of 0.6-1.9 g/day, or the range of 0.65-1.85 g/day, or the range of 0.7-1.8 g/day, or the range of 0.75-1.75 g/day, or the range of 0.8-1.7 g/day, or the range of 0.85-1.65 g/day, or the range of 0.9-1.6 g/day, or the range of 0.95-1.55 g/day, or the range of 1-1.5 g/day, or the range of 1.05-1.45 g/day, or the range of 1.1-1.4 g/day, or the range of 1.15-1.35 g/day, or the range of 1.2-1.3 g/day, or the range of 1.23-1.25 g/day.

An embodiment of a fourth aspect of the present invention provides a chemotherapeutic drug for treating small cell lung cancer, including a pharmaceutically effective amount of a compound of the general formula I or a pharmaceutically acceptable salt thereof or a corresponding effective amount of a targeted drug delivery system. The pharmaceutically effective amount of the drug may be determined by a person skilled in the art according to patient's conditions, being in the range of 0.5-2 g/day, optionally in the range of 0.55-1.95 g/day, or the range of 0.6-1.9 g/day, or the range of 0.65-1.85 g/day, or the range of 0.7-1.8 g/day, or the range of 0.75-1.75 g/day, or the range of 0.8-1.7 g/day, or the range of 0.85-1.65 g/day, or the range of 0.9-1.6 g/day, or the range of 0.95-1.55 g/day, or the range of 1-1.5 g/day, or the range of 1.05-1.45 g/day, or the range of 1.1-1.4 g/day, or the range of 1.15-1.35 g/day, or the range of 1.2-1.3 g/day, or the range of 1.23-1.25 g/day.

An embodiment of a fifth aspect of the present invention provides a method for preparing a compound of the general formula I or a pharmaceutically acceptable salt thereof, including a step of performing anhydride acylation from N-(2-chloro-4-nitrophenyl)-5-chloro-2-hydroxybenzamide and the acylation is catalyzed by 4-dimethylaminopyridine.

In this embodiment, the method also includes a step of preparing N-(2-chloro-4-nitrophenyl)-5-chloro-2-hydroxybenzamide by condensation between 5-chlorosalicylic acid and 2-chloro-4-nitroaniline. In this embodiment, the anhydride is used and preferred to be acetic anhydride.

DETAILED DESCRIPTION OF THE PREFERRED EMBODIMENTS

Figure 1:
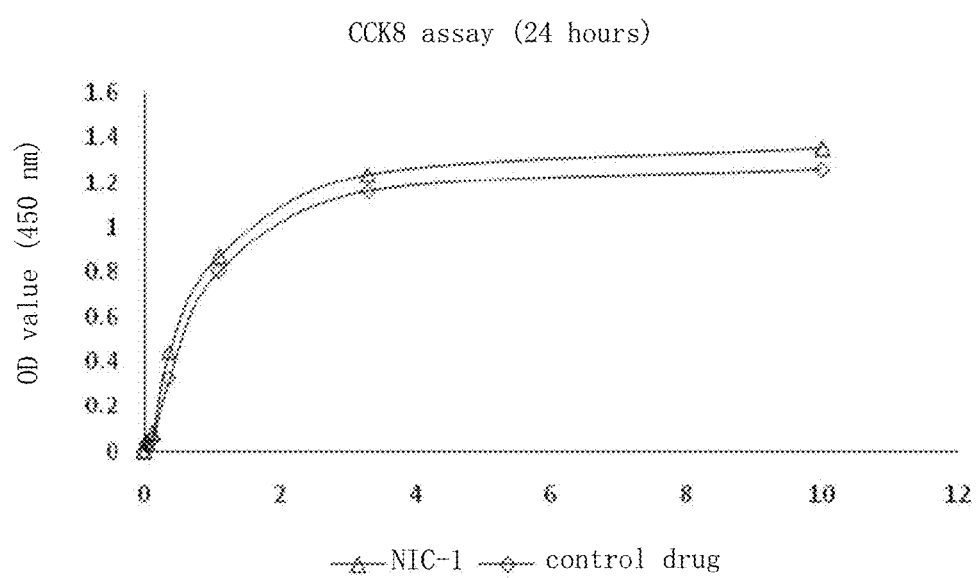
FIG. 1 is a chart of comparison of the inhibitory effect of a synthesized compound NIC-1 (0.041 μM-3.3 μM) according to the present invention on the cell viability of a Jurkat cell suspension after 24-hour culture with respect to a control drug N-(2-chloro-4-nitrophenyl)-5-chloro-2-hydroxybenzamide and a blank control, wherein the horizontal coordinate represents a drug concentration for administration, and the vertical coordinate represents a difference in optical density (OD) between the test drug and the blank control with no drug given.

The compound of the present invention may have a center of asymmetry, chiral axes and chiral planes, and racemates, racemate mixtures and single diastereomers that are present and all possible isomers and mixtures thereof, including optical isomers, all come within the scope of the present invention. Further, the compound disclosed herein may exist as a tautomer, and both tautomeric forms are included within the scope of the present invention even if only one of them is described herein.

It should be understood that any numerical value recited herein includes from a lower limit to an upper limit. For example, if the range of concentration is described as 1%-50%, it means that values such as 2%-40%, 10%-30% or 1%-3% are expressly listed herein. These are merely illustrative of particular examples, and all possible combinations of numerical values between the minimum value and the maximum value are considered to be expressly stated herein.

Moreover, it should be understood that the words and terms used herein are intended for illustrative purposes only rather than limiting.

Definitions

As used herein, the term "pharmaceutically acceptable salt" refers to that, for example, if the compound of the present invention is alkaline, it reacts with an inorganic or organic acid to form a conventional non-toxic salt of the compound of the present invention, including, for example, a salt derived from an inorganic acid such as hydrochloric acid, hydrobromic acid, sulfuric acid, sulfamic acid, phosphoric acid and nitric acid; also including a salt derived from an organic acid such as acetic acid, propionic acid, succinic acid, glycolic acid, lactic acid, oxalic acid, malic acid, tartaric acid, citric acid, embonic acid, maleic acid, hydroxymaleic acid, salicylic acid, stearic acid, phenylacetic acid, glutamic acid, benzoic acid, sulfanilic acid, 2-acetoxybenzoic acid, fumaric acid, toluenesulfonic acid, methanesulfonic acid, ethanedisulfonic acid, hydroxyethylsulfonic acid, and trifluoroacetic acid; and if the compound of the present invention is acidic, it reacts with a pharmaceutically acceptable non-toxic alkali (including an inorganic alkali and an organic alkali) to form a salt, including an aluminum salt, a calcium salt, an ammonium salt, an iron salt, a ferrous salt, a potassium salt, a sodium salt, a zinc salt, a copper salt, a lithium salt, a magnesium salt, a manganese salt, and a manganous salt; preferably an ammonium salt, a calcium salt, a magnesium salt, a potassium salt and a sodium salt, also including a pharmaceutically acceptable salt derived from an organic non-toxic alkali; and the alkali includes a salt of primary, secondary and tertiary amines, substituted amines including natural substituted amines, cyclic amines and alkaline ion exchange resins such as arginine, betaine, caffeine, choline, N,N'-dibenzylethylenediamine, diethylamine, 2-diethylaminoethanol, 2-dimethylaminoethanol, aminoethanol, ethanolamine, ethylenediamine, N-ethylmorpholine, N-ethylpiperidine, glucosamine, dextrosamine, histidine, hydroxocobalamin, isopropylamine, lysine, methylglucamine, morpholine, piperazine, piperidine, polyamine resin, procaine, purine, theobromine, triethylamine, trimethylamine, tripropylamine, tromethamine, etc.

As used herein, the term "targeted drug delivery system (TDDS)" has the similar meaning to "targeted preparations", and refers to a drug delivery system such that a drug is selectively concentrated and located in target tissues, target organs, target cells or intracellular structures by local administration or systemic blood circulation using a drug carrier. The mechanism is that the drug may be adsorbed closely on the carrier due to low solubility and then delivered to a tumor mass more efficiently under the passive and active targeting actions of the carrier, thereby reducing toxic side effects and improving effectiveness. The targeted drug delivery system is featured by targeted concentration, controlled drug release, no toxicity and biodegradability. A targeted drug delivery system, as a fourth generation dosage form, has high effectiveness and less toxic side effects, and is considered as a suitable dosage form for anticancer drugs. Various types of targeted drug delivery system include passive targeting preparations, active targeting preparations, physicochemical targeting preparations, and the like. Based on carrier types, the targeted preparations may be divided into liposomes, millimicro-particles, millimicro-spheres, complex emulsions, and the like. The route of administration of the targeted drug delivery system includes an oral drug delivery system, a rectal drug delivery system, a colon drug delivery system, a nasal drug delivery system, a skin drug delivery system, a topical or systemic blood circulation drug delivery system, an ophthalmic drug delivery system, and the like. Based on target sites, the targeted drug delivery system may be divided into liver targeting preparations, lung targeting preparations, and the like. Currently, the drug delivery system targeting the lung includes liposomes, emulsions, solid lipid nanoparticles, microparticles, nanoparticles, and the like.

As used herein, the term "effective amount" or "pharmaceutically effective amount" refers to a dose of a compound or composition effective in producing a desired effect. As used herein, this term also refers to an effective amount that produces a desired in vivo effect in an animal, preferably a human being, for example, disease treatment. The pharmaceutically effective amount of the drug may be determined by a person skilled in the art according to patient's conditions, being in the range of 0.5-2 g/day, optionally in the range of 0.55-1.95 g/day, or the range of 0.6-1.9 g/day, or the range of 0.65-1.85 g/day, or the range of 0.7-1.8 g/day, or the range of 0.75-1.75 g/day, or the range of 0.8-1.7 g/day, or the range of 0.85-1.65 g/day, or the range of 0.9-1.6 g/day, or the range of 0.95-1.55 g/day, or the range of 1-1.5 g/day, or the range of 1.05-1.45 g/day, or the range of 1.1-1.4 g/day, or the range of 1.15-1.35 g/day, or the range of 1.2-1.3 g/day, or the range of 1.23-1.25 g/day.

As used herein, the term "treating or treatment" refers to a disorder treatment, generally involving a treatment or therapy for achieving a desired therapeutic effect, regardless of the subject being a human being or an animal (for example, in veterinary applications). For example, treating or treatment includes prevention and amelioration or improvement of a disorder, disease or symptom, alternatively, treating or treatment can inhibit the progression of a disorder or disease (for example, slowing the progression of a disease/symptom or suppressing the progression of a disease/symptom).

As used herein, "acylation" refers to an organic chemical reaction in which hydrogen or another group is substituted by an acyl group in an acyl-providing compound, and as the acylation of a phenolic hydroxyl group is more difficult than alcohols because of the decrease in nucleophilicity of oxygen atom in a hydroxyl group due to the influence of aromatic hydrocarbons, an acylation catalyst is also included in addition to an acylation agent commonly used for O-acylation of alcohols and phenols, well known by a person skilled in the art, such as carboxylic acids, carboxylic acid esters, acid anhydrides, acid chlorides and ketenes, thereby reducing the temperature required for acylation reaction.

An acylation catalyst used herein includes a protic acid, such as an organic acid (benzenesulfonic acid, p-toluenesulfonic acid); an Lewis acid, such as boron trifluoride ($BF_3$), aluminum chloride ($AlCl_3$), zinc chloride ($ZnCl_2$), and silica gel; a strong acid type ion exchange resin; dicyclohexylcarbodiimide (DCC) and its analogues; and a strongly nucleophilic acylation catalyst, such as 4-dimethylaminopyridine (DMAP). The use of a strongly nucleophilic acylation catalyst, such as 4-dimethylaminopyridine (DMAP), is particularly advantageous for reducing the temperature required for acylation reaction, reducing the conditions required for the reaction, reducing the test cost and increasing the reaction efficiency.

As described above in the first aspect, the present invention specifically provides a novel compound or a pharmaceutically acceptable salt thereof, characterized in that the compound has the general formula I:

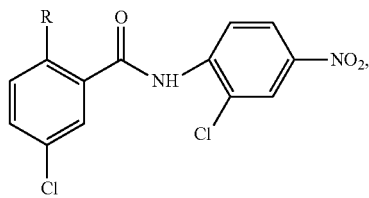

wherein R is an acyloxy group selected from acetoxy, propionyloxy or acryloyloxy. The molecular weight of such compound is in the range of 367-382.

An optional embodiment of the present invention is that the acyloxy group is acetoxy, and the compound is N-(2-chloro-4-nitrophenyl)-5-chloro-2-acetoxybenzamide, the nuclear magnetic resonance NMR spectrum being:

$^1$HNMR (400 MHz, $CDCl_3$) δ9.03 (s, 1H), 8.85 (d, 1H, J=8.0 Hz), 8.34 (s, 1H), 8.20-8.24 (dd, 2H, J=8.0 Hz, J=4.0 Hz), 7.96 (d, 1H, J=2.4 Hz), 7.52-7.56 (dd, 2H, J=8.0 Hz, J=4.0 Hz), 7.15, 7.18 (d, 1H, J=12.0 Hz), 2.36 (s, 3H).

The molecular weight of such compound is in the range of 367-368.

According to experimental results, it is found that the compound is slightly soluble in ethanol and ether, soluble in dichloromethane and insoluble in water.

The melting point of the compound is greater than 200° C.

A second aspect of the present invention provides use of a compound of the general formula I or a pharmaceutically acceptable salt thereof for the preparation of a chemotherapeutic drug for treating small cell lung cancer.

In this embodiment, the chemotherapeutic drug for treating small cell lung cancer includes a targeted drug delivery system, and the targeted drug delivery system is a targeted drug carrier-encapsulated dosage form selected from liposomes, millimicro-particles, millimicro-spheres, micro-particles, nano-particles, complex emulsions, or solid lipid nano-particles, preferably a targeted drug carrier-encapsulated dosage form of complex emulsions or solid lipid nano-particles.

The chemotherapeutic drug containing the compound for treating small cell lung cancer can be used as a drug against small cell lung cancer as well as a second-line cancer treatment drug against a relapsed cancer. The cancer includes a respiratory cancer, such as small cell lung cancer, non-small cell lung cancer, bronchial adenocarcinoma, pleuropulmonary blastoma, etc.

A third aspect of the present invention provides a targeted drug delivery system characterized by including a pharmaceutically effective amount of a compound of the general formula I or a pharmaceutically acceptable salt thereof, and the targeted drug delivery system is a targeted drug carrier-encapsulated dosage form selected from liposomes, millimicro-particles, millimicro-spheres, micro-particles, nano-particles, complex emulsions, or solid lipid nano-particles, preferably a targeted drug carrier-encapsulated dosage form of complex emulsions or solid lipid nano-particles. The pharmaceutically effective amount of the drug may be determined by a person skilled in the art according to patient's conditions, being in the range of 0.5-2 g/day, optionally in the range of 0.55-1.95 g/day, or the range of 0.6-1.9 g/day, or the range of 0.65-1.85 g/day, or the range of 0.7-1.8 g/day, or the range of 0.75-1.75 g/day, or the range of 0.8-1.7 g/day, or the range of 0.85-1.65 g/day, or the range of 0.9-1.6 g/day, or the range of 0.95-1.55 g/day, or the range of 1-1.5 g/day, or the range of 1.05-1.45 g/day, or the range of 1.1-1.4 g/day, or the range of 1.15-1.35 g/day, or the range of 1.2-1.3 g/day, or the range of 1.23-1.25 g/day.

A fourth aspect of the present invention provides a chemotherapeutic drug for treating small cell lung cancer, including a pharmaceutically effective amount of a compound of the general formula I or a pharmaceutically acceptable salt thereof or a corresponding effective amount of a targeted drug delivery system, and the chemotherapeutic drug may be a targeted drug carrier-encapsulated dosage form selected from liposomes, millimicro-particles, millimicro-spheres, micro-particles, nano-particles, complex emulsions, or solid lipid nano-particles. The pharmaceutically effective amount of the drug may be determined by a person skilled in the art according to patient's conditions, being in the range of 0.5-2 g/day, optionally in the range of 0.55-1.95 g/day, or the range of 0.6-1.9 g/day, or the range of 0.65-1.85 g/day, or the range of 0.7-1.8 g/day, or the range of 0.75-1.75 g/day, or the range of 0.8-1.7 g/day, or the range of 0.85-1.65 g/day, or the range of 0.9-1.6 g/day, or the range of 0.95-1.55 g/day, or the range of 1-1.5 g/day, or the range of 1.05-1.45 g/day, or the range of 1.1-1.4 g/day, or the range of 1.15-1.35 g/day, or the range of 1.2-1.3 g/day, or the range of 1.23-1.25 g/day.

A fifth aspect of the present invention provides a method for preparing a compound of the general formula I or a pharmaceutically acceptable salt thereof, specifically including a step of performing anhydride acylation from N-(2-chloro-4-nitrophenyl)-5-chloro-2-hydroxybenzamide under catalytic acylation with 4-dimethylaminopyridine (DMAP).

Further, in the preparation method, the acid anhydride is acetic anhydride. This synthesis step may be represented as follows:

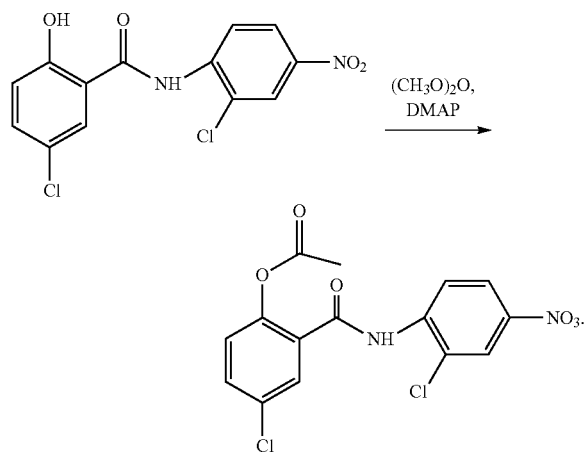

An optional embodiment of the present invention is that the method also includes a step of preparing N-(2-chloro-4-nitrophenyl)-5-chloro-2-hydroxybenzamide from 5-chlorosalicylic acid and 2-chloro-4-nitroaniline.

This synthesis step may be represented as follows:

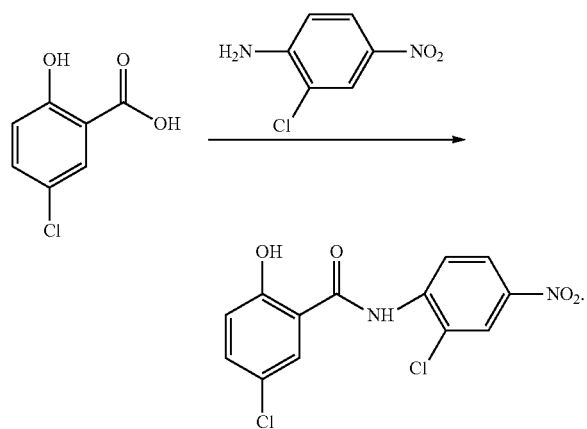

Moreover, the method for preparing a compound of the general formula I or a pharmaceutically acceptable salt thereof according to the present invention is advantageous in that the reagents and materials are easily accessible and the method has simple synthesis steps, while the obtained compound of the general formula I shows surprising outcomes in the study of the drug in small cell lung cancer cell line, as described in the embodiments below, showing the results of in vitro cell colony formation assay and cell viability inhibition assay of the drug against small cell lung cancer cell line. The compound of the general formula I according to the invention, in a certain concentration, can completely inhibit the growth of small cell lung cancer cells H446, with no colony formation; as compared to the control drug N-(2-chloro-4-nitrophenyl)-5-chloro-2-hydroxybenzamide that has the similar structure as the compound, the compound can more effectively inhibit the growth of small cell lung cancer cells; and as compared to the drug for first-line treatment of small cell lung cancer, the compound can more effectively inhibit the growth of small cell lung cancer cells.

N-(2-chloro-4-nitrophenyl)-5-chloro-2-hydroxybenzamide can be clinically used in oral treatment of taeniasis disease, with occasional side effects manifested by fatigue, dizziness, chest tightness, gastrointestinal disorders, fever and itching, and can be given to adults as well as children at a lower dose, indicating that it has less toxic effects on human body. Thus, the compound of the general formula I synthesized by the present invention, having a structure similar to the control drug as N-(2-chloro-4-nitrophenyl)-5-chloro-2-hydroxybenzamide, when used in treatment of small cell lung cancer, is excellent in high effectiveness and less toxic side effects after administration.

Further, as understood by a person skilled in the art for targeted drug delivery systems, the targeted drug carrier-encapsulated dosage forms that contain the compound of the general formula I or a pharmaceutically acceptable salt thereof and are selected from liposomes, millimicro-particles, millimicro-spheres, micro-particles, nanoparticles, complex emulsions or solid lipid nanoparticles can be developed, and the therapeutic effect on small cell lung cancer may be confirmed by the experimental data described below.

Moreover, as understood by a person skilled in the art for chemotherapeutic drugs, the targeted drug delivery systems of the targeted drug carrier-encapsulated dosage forms that contain the compound of the general formula I or a pharmaceutically acceptable salt thereof and are selected from liposomes, millimicro-particles, millimicro-spheres, micro-particles, nanoparticles, complex emulsions or solid lipid nanoparticles can be developed, and the therapeutic effect on small cell lung cancer may also be confirmed by the experimental data described below.

EXAMPLES

The present invention will be specifically described below with reference to examples. Although the following examples further provide detailed descriptions of some embodiments of the present invention, these examples should be considered as illustrative only and not to limit the invention as defined by the appended claims in any way. Various modifications and improvements may be made by a person skilled in the art without departing from the teachings of the present invention.

Synthesis Step 1: Preparation of N-(2-chloro-4-nitrophenyl)-5-chloro-2-hydroxybenzamide Preparation Example 1

A solution of $PCl_3$ (2.4 g, 17.5 mmol) dissolved in chlorobenzene was dropwise added into a solution of 5-chlorosalicylic acid (3.44 g, 20.0 mmol) and 2-chloro-4-nitroaniline (3.44 g, 20.0 mmol) dissolved in chlorobenzene at 135° C. After 3 hours, the reaction solution was cooled down to room temperature. The resulting solid from filtration was collected and washed with water and then recrystallized from ethyl acetate (or acetone) to obtain N-(2-chloro-4-nitrophenyl)-5-chloro-2-hydroxybenzamide in a form of white solid (6.8 g, 68.7%).

Preparation Example 2

A solution (0.83 mL, 1.67 mmol) of 2.0 M $PCl_3$ in $CH_2Cl_2$ was added, in a dropwise manner, into a solution of 5-chlorosalicylic acid (0.72 g, 4.17 mmol) and 2-chloro-4-nitroaniline (0.72 g, 4.17 mmol) after being dissolved and boiled in xylene (10 mL). After 2 hours, the reaction solution was transferred to a beaker with a pipette, rapidly stirred and cooled down to room temperature. The product was separated to obtain an off-white crystal. The crude product was recrystallized from ethyl acetate to obtain pure N-(2-chloro-4-nitrophenyl)-5-chloro-2-hydroxybenzamide in a form of white solid.

Synthesis Step 2: Synthetic Preparation of N-(2-chloro-4-nitrophenyl)-5-chloro-2-acetoxybenzamide Preparation Example 3

Acetic anhydride was dropwise added into a solution (0.66 g, 2.0 mmol) of N-(2-chloro-4-nitrophenyl)-5-chloro-2-hydroxybenzamide and a solution (0.12 g, 1.0 mmol) of 4-dimethylaminopyridine DMAP in dichloromethane. The mixture was left at room temperature for 18 hours. The reaction mixture was diluted with dichloromethane and extracted with water.

The organic fraction was washed with brine, dried over anhydrous sodium sulfate, and concentrated to obtain a crude product. The crude product was allowed to pass through a silica gel column (petroleum ether/ethyl acetate=1/0 to 40/1) to remove residues. Pure N-(2-chloro-4-nitrophenyl)-5-chloro-2-acyloxybenzamide (NIC-1) was obtained.

The results of NMR spectrum assay showed: $^1$HNMR (400 MHz, $CDCl_3$) δ9.03 (s, 1H), 8.85 (d, 1H, J=8.0 Hz), 8.34 (s, 1H), 8.20-8.24 (dd, 2H, J=8.0 Hz, J=4.0 Hz), 7.96 (d, 1H, J=2.4 Hz), 7.52-7.56 (dd, 2H, J=8.0 Hz, J=4.0 Hz), 7.15, 7.18 (d, 1H, J=12.0 Hz), 2.36 (s, 3H).

According to experimental results, it is found that the compound is slightly soluble in ethanol and ether, soluble in dichloromethane and insoluble in water. The molecular weight is 367.9967.

Cell Drug Experiments

Experiment 1 Cytological Experiment of NIC-1 Against Small Cell Lung Cancer

Test cell line: Jurkat cell line (purchased from Nanjing Cobioer Co., Ltd.)

Experimental method: Cell viability CCK-8 assay

Experimental design: within a dose concentration range of 0.041 μM-10 μM, six concentrations were designed with three-fold increments, including 0.041 μM, 0.123 μM, 0.367 μM, 1.1 μM, 3.3 μM and 10 μM.

Experimental Reagents and Materials:

cell counting kit-8 (CCK-8, batch No. GX733, code: CK04, manufactured by Dojindo Japan)

96-well plate (Costar 96-well non-detachable elisa plate, produced by Corning Incorporated company)

Experimental Process:

1. A Jurkat cell suspension was prepared and inoculated to the 96-well plate at an amount of $5 \times 10^4$/well.

2. The Jurkat cell suspension was directly added to different concentrations of NIC-1 and control drug N-(2-chloro-4-nitrophenyl)-5-chloro-2-hydroxybenzamide, followed by culture in an incubator at 37° C. for 24 h, 48 h and 72 h respectively; CCK8 was measured by adding CCK8 to each well at an amount of 10 μl/well, culturing for 2-3 h and detecting a value of OD at 450 nm using a microplate reader.

Figure 2:
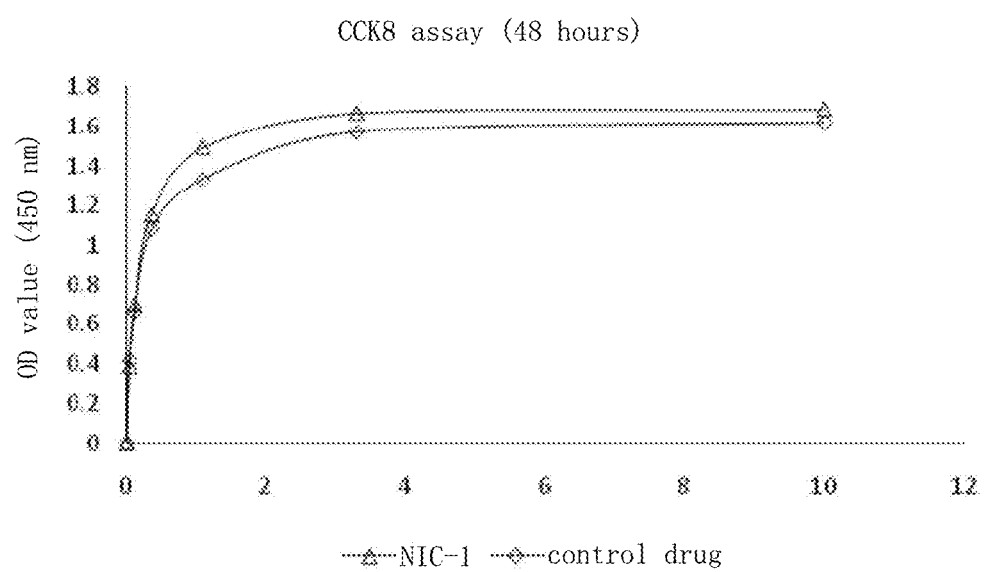
FIG. 2 is a chart of comparison of the inhibitory effect of a synthesized compound NIC-1 (0.041 μM-10 μM) according to the present invention on the cell viability of a Jurkat cell suspension after 48-hour culture with respect to a control drug N-(2-chloro-4-nitrophenyl)-5-chloro-2-hydroxybenzamide and a blank control, wherein the horizontal coordinate represents a drug concentration for administration, and the vertical coordinate represents a difference in OD between the test drug and the blank control with no drug given.
Figure 3:
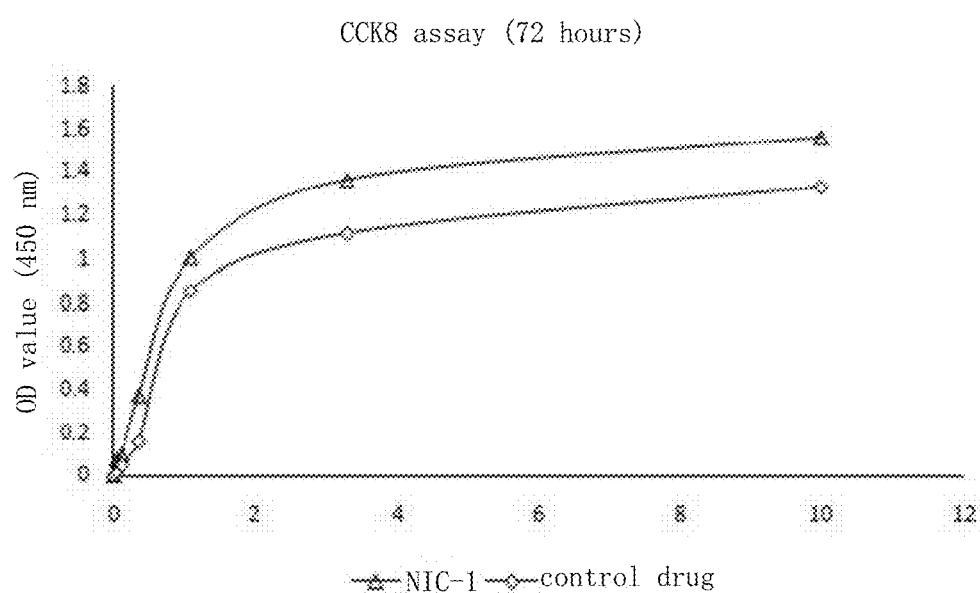
FIG. 3 is a chart of comparison of the inhibitory effect of a synthesized compound NIC-1 (0.041 μM-10 μM) according to the present invention on the cell viability of a Jurkat cell suspension after 72-hour culture with respect to a control drug N-(2-chloro-4-nitrophenyl)-5-chloro-2-hydroxybenzamide and a blank control, wherein the horizontal coordinate represents a drug concentration for administration, and the vertical coordinate represents a difference in OD between the test drug and the blank control with no drug given.

Experimental results: the outcomes of the synthesized compound NIC-1 of the present invention and the control drug N-(2-chloro-4-nitrophenyl)-5-chloro-2-hydroxybenzamide in the six concentrations were compared with those of the blank control, respectively. As shown in FIGS. 1-3, a chart of comparison of the inhibitory effect on the cell viability of Jurkat cell line was shown in each figure, wherein the horizontal coordinate represented a drug concentration for administration, and the vertical coordinate represented a difference in OD between the test drug and the blank control with no drug given.

The Jurkat cell line was treated with NIC-1 and control drug N-(2-chloro-4-nitrophenyl)-5-chloro-2-hydroxybenzamide for 24 h, 48 h and 72 h, followed by detection of cell viability with CCK-8 assay. The results showed the compound in any of the six concentrations was superior to the control drug N-(2-chloro-4-nitrophenyl)-5-chloro-2-hydroxybenzamide. Accordingly, the inhibitory effect of NIC-1 on tumor cell growth was significantly better than that of the control drug N-(2-chloro-4-nitrophenyl)-5-chloro-2-hydroxybenzamide.

Experiment 2 Cytological Experiment of NIC-1 Against Small Cell Lung Cancer

Test cell line: small cell lung cancer cell line H446 (purchased from Shanghai Beinuo Life Science Co., Ltd.)

Experimental method: H446 cell colony in vitro formation assay

Experimental reagent: crystal violet stain solution (batch No. C0121, manufactured by Beyotime company)

Detection method: crystal violet staining

Experimental Design:

Based on the document 'A retrospective study of first-line treatment of extensive-stage small cell lung cancer using topotecan as compared with etoposide plus cisplatin' mentioned above, as the first-line treatment of small cell lung cancer typically utilizes combined chemotherapy of etoposide and cisplatin, etoposide (vp-16) is adopted in design experiment for efficacy comparison.

Experimental Process:

On Day 1, a 6-well plate (Transwell, batch No. 3428, manufactured by Corning Incorporated) was adopted as cell plate, with 2000 cells/well per plate.

On Day 2, after microscopic observation of cell adherence, a 1 ml medium containing the drug was loaded to each well, with settings of 2 wells in one group and totally three groups: A. 6 μmol/L, a. 6 μmol/L (multiple wells); B. blank (no drug); b. blank (no drug, multiple wells); C. 12 μmol/L; c. 12 μmol/L (multiple wells); the drugs were changed every three days, and the observation was performed every day.

On Day 7, cell colonies were visually observed at the bottom of the vessel, and the cells were collected by:
discarding the culture medium in each well,
washing cells with phosphate buffered saline (PBS) twice for 5 minutes each time,
adding 500 μl crystal violet stain solution to each well for staining at room temperature for 15 minutes,
washing cells with PBS twice for 5 minutes each time,
and finally detecting on a WB analyzer.

Figure 4:
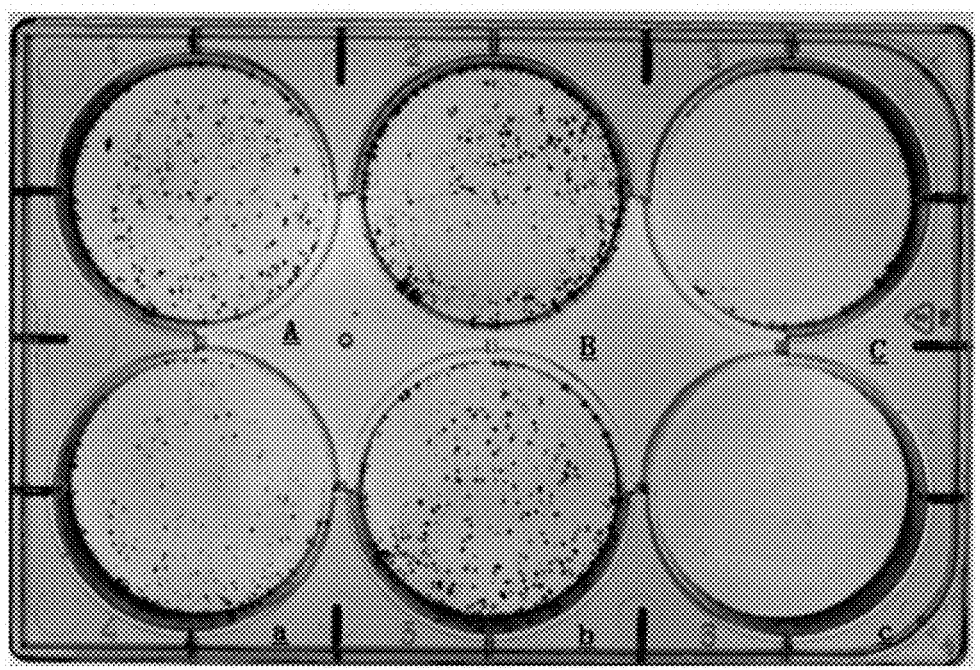
FIG. 4 is a graph of in vitro cell colony formation assay within one week of the inhibition of a synthesized compound NIC-1 according to the present invention in small cell lung cancer cell line H446. The dose concentrations for each well are as follows: A. 6 μmol/L, a. 6 μmol/L (multiple wells), B. blank (no drug given) b. blank (no drug given, multiple wells); C. 12 μmol/L, c. 12 μmol/L (multiple wells).
Figure 5:
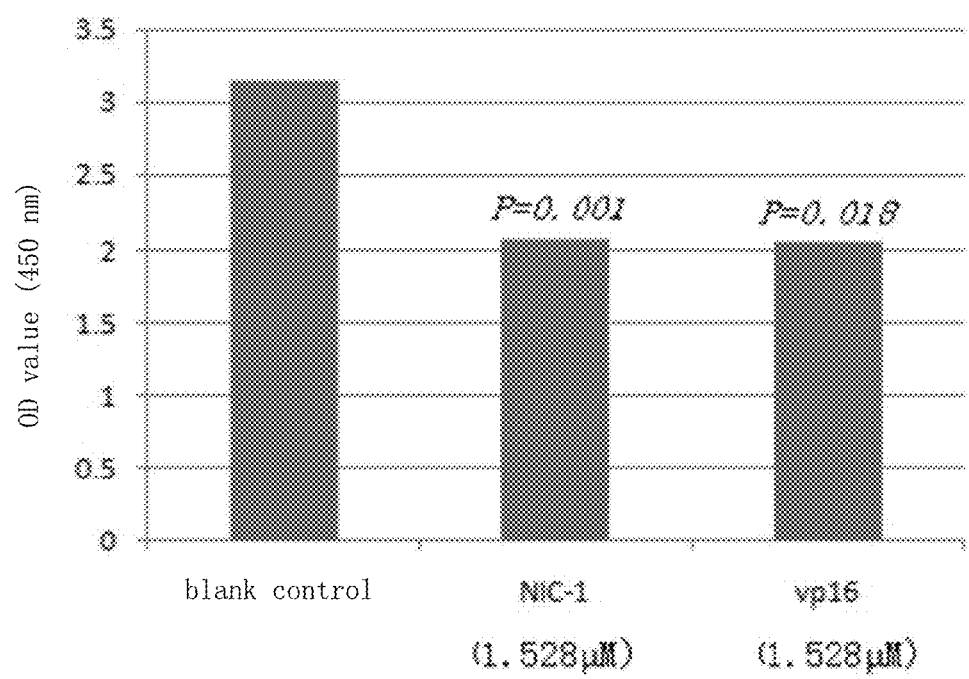
FIG. 5 is a chart of comparison of the inhibitory effect of a synthesized compound NIC-1 (1.528 μM) according to the present invention on the cell viability of small cell lung cancer cell line H446 after 48-h culture with respect to etoposide (vp16) and a blank control, wherein the horizontal axis represents the blank control, NIC-1, vp-16 and corresponding dosage concentrations, and the vertical axis represents measured values of OD.
Figure 6:
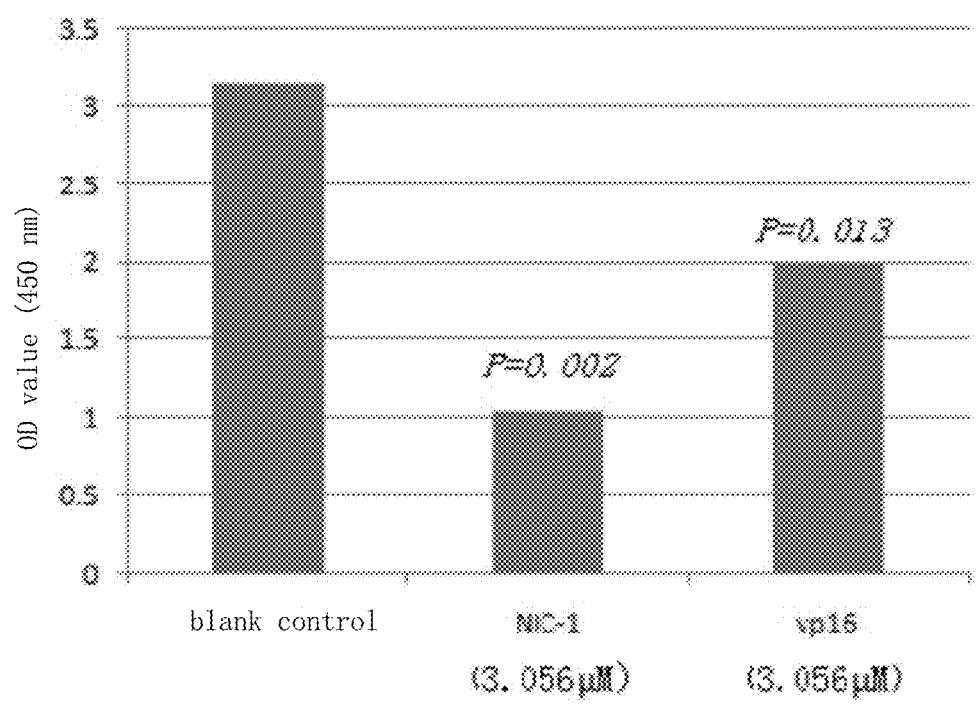
FIG. 6 is a chart of comparison of the inhibitory effect of a synthesized compound NIC-1 (3.056 μM) according to the present invention on the cell viability of small cell lung cancer cell line H446 after 48-h culture with respect to etoposide (vp16) and a blank control, wherein the horizontal axis represents the blank control, NIC-1, vp-16 and corresponding dosage concentrations, and the vertical axis represents measured values of OD.
Figure 7:
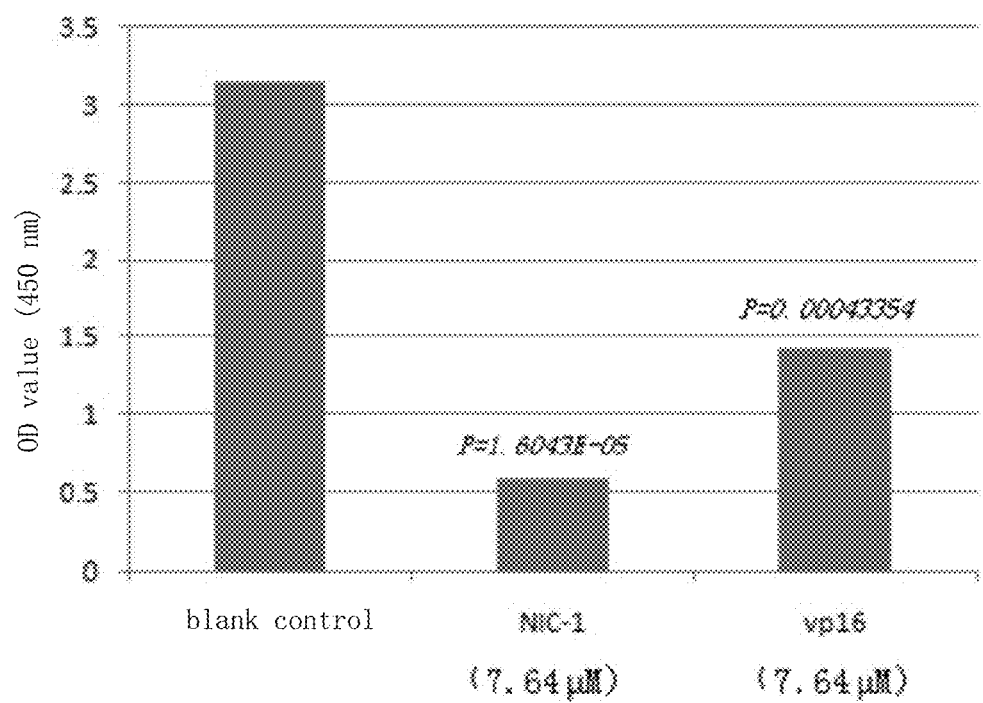
FIG. 7 is a chart of comparison of the inhibitory effect of a synthesized compound NIC-1 (7.64 μM) according to the present invention on the cell viability of small cell lung cancer cell line H446 after 48-h culture with respect to etoposide (vp16) and a blank control, wherein the horizontal axis represents the blank control, NIC-1, vp-16 and corresponding dosage concentrations, and the vertical axis represents measured values of OD.
Figure 8:
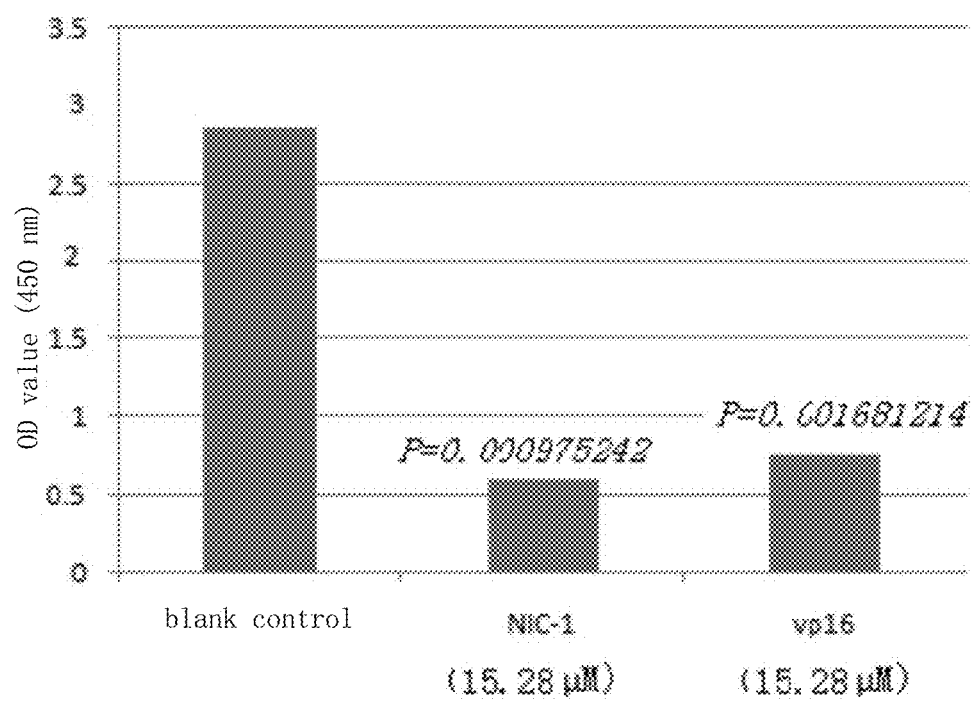
FIG. 8 is a chart of comparison of the inhibitory effect of a synthesized compound NIC-1 (15.28 μM) according to the present invention on the cell viability of small cell lung cancer cell line H446 after 48-h culture with respect to etoposide (vp16) and a blank control, wherein the horizontal axis represents the blank control, NIC-1, vp-16 and corresponding dosage concentrations, and the vertical axis represents measured values of OD.

Experimental results: the results of in vitro colony formation assay of NIC-1 against small cell lung cancer is as shown in FIG. 4, and the experiment lasted for one week. The results showed that on Day 7 (one week), NIC-1 in the concentration of 6 μmol/L partially inhibited the growth of small cell lung cancer H446 cells, NIC-1 in the concentration of 12 μmol/L completely inhibited the growth of small cell lung cancer H446 cells, with no colony formation, indicating that NIC-1 has good inhibitory effect on the growth of small cell lung cancer cells.

Experiment 3 Cytological Experiment of NIC-1 Against Small Cell Lung Cancer

Test cell line: small cell lung cancer cell line H446 (purchased from Shanghai Beinuo Life Science Co., Ltd.)

Experimental Method:

Cell viability CCK-8 assay: CCK8 assay, with a reagent containing 2-(2-methoxy-4-nitrophenyl)-3-(4-nitrophenyl)-5-(2,4-disulfophenyl)-2H-tetrazole monosodium salt (WST-8), is reduced by dehydrogenase in the cells in the presence of electron carrier 1-methoxy-5-methylphenazinium sulfoxide (1-Methoxy PMS), to obtain a highly water-soluble yellow formazan product (Formazan), and the count of viable cells is positively associated with the amount of obtained formazan product. Thus, CCK8 assay can be directly used for the evaluation of cell proliferation and toxicity analysis.

Experimental Reagents and Materials:

Cell counting kit-8 (CCK-8, batch No. GX733, code: CK04, manufactured by Dojindo Japan)

96-well plate (Costar 96-well non-detachable elisa plate, produced by Corning Incorporated company)

Experimental Process:

Each well of 96-well plate was loaded at an amount of $7 \times 10^3$ cells/well. After 24 h plating, 200 µl of solution was supplied to each well. NIC-1, vp-16 and blank were applied to the plate in four concentrations: concentration 1=1.528 µm, concentration 2=1.528 µm*2, concentration 3=1.528 µm*5, concentration 4=1.528 µm*10, wand each group was made in triplicate.

The plate was harvested 48 h after dosing, by:

discarding 200 µl solution in each well, adding 100 µl solution (90 µl medium+10 µl CCK8 stock solution) to each well, placing the plate in a 37° C. incubator for about 1 hour, and measuring a value of OD at 450 nm using a microplate reader.

Experimental Results:

The small cell lung cancer cell line H446 was treated with NIC-1 and etoposide (vp16) for 45 h respectively, and then the cell viability was detected by CCK-8 assay.

The synthesized compound NIC-1 of the present invention in the concentrations of 1.528 µM, 3.056 µM, 7.64 µM and 15.28 µM was compared with etoposide (vp16) and blank control, respectively. As shown in FIGS. 5-8, a chart of comparison of the inhibitory effect on the cell viability of small cell lung cancer cell line H446 was shown in each figure, wherein the horizontal axis represented the blank control, NIC-1, vp-16 and corresponding dosage concentrations, and the vertical axis represented measured OD values.

The p-value reflecting data reliability was marked on each bar graph. As shown in FIGS. 5-8, the P-values for the NIC-1 group were all less than 0.005, and the P-values for the vp16 group were all less than 0.02, indicating that the data were reliable.

The results showed that NIC-1 had inhibitory effect on cell line H446, and was slightly better than etoposide (vp16) at the concentration of 1.528 µM, and significantly better than etoposide (vp16) at all concentrations of 3.06 µM, 7.64 µM and 15.28 µM. Accordingly, NIC-1 has good inhibitory effect on the growth of small cell lung cancer cells, generally better than etoposide.

The invention claimed is:

1. A method of inhibiting small cell lung cancer cell line H446 proliferation comprising administering of an effective amount of a compound or pharmaceutically acceptable salt thereof to said cell line,
wherein the compound has the general formula I,

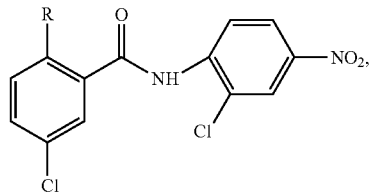

and R is an acyloxy group selected from acetoxy, propionyloxy or acryloyloxy.

2. The method according to claim 1, characterized in that the acyloxy group is acetoxy.

3. The method according to claim 1, characterized in that the compound has a molecular weight from 367 to 382 g/mol.

4. The method according to claim 3, characterized in that the compound has a molecular weight from 367 to 368 g/mol.

5. A method of treating small cell lung cancer, comprising administering to a patient of small cell lung cancer an effective amount of a compound or pharmaceutically acceptable salt thereof,
wherein the compound has the general formula I,

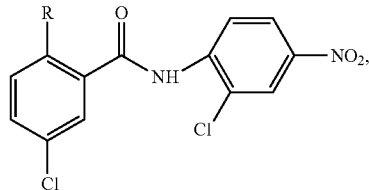

and R is an acyloxy group selected from acetoxy, propionyloxy or acryloyloxy.

6. The method according to claim 5, characterized in that the acyloxy group is acetoxy.

7. The method according to claim 5, characterized in that the compound has a molecular weight from 367 to 382 g/mol.

8. The method according to claim 7, characterized in that the compound has a molecular weight from 367 to 368 g/mol.

9. The method according to claim 5, characterized in that performing the method of treating small cell lung cancer in a target drug delivery system.

10. The method according to claim 9, characterized in that the target drug delivery system is a target drug carrier-encapsulated dosage form selected from liposomes, milli-micro-particles, millimicro-spheres, micro-particles, complex emulsions, or solid lipid nano-particles.

11. The method according to claim 9, characterized in that the targeted drug delivery system is of a type selected from passive targeting preparations, active targeting preparations or physicochemical targeting preparations.

12. The method according to claim 9, characterized in that the target drug delivery system has a route of administration selected from oral drug delivery systems, rectal drug.

* * * * *